United States Patent
Luo

(10) Patent No.: US 11,926,772 B2
(45) Date of Patent: Mar. 12, 2024

(54) HIGH-PERFORMANCE SKY BLUE THERMALLY ACTIVATED DELAYED FLUORESCENT MATERIAL, MANUFACTURING METHOD THEREOF, AND APPLICATION THEREOF

(71) Applicant: WUHAN CHINA STAR OPTOELECTRONICS SEMICONDUCTOR DISPLAY TECHNOLOGY CO., LTD., Wuhan (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 777 days.

(21) Appl. No.: 16/979,847

(22) PCT Filed: May 14, 2020

(86) PCT No.: PCT/CN2020/090216
§ 371 (c)(1),
(2) Date: Sep. 10, 2020

(87) PCT Pub. No.: WO2021/135035
PCT Pub. Date: Jul. 8, 2021

(65) Prior Publication Data
US 2023/0096584 A1    Mar. 30, 2023

(30) Foreign Application Priority Data

Jan. 3, 2020  (CN) .......................... 202010004429.3

(51) Int. Cl.
| | | |
|---|---|---|
| *C09K 11/06* | (2006.01) | |
| *C07D 409/10* | (2006.01) | |
| *C07D 413/10* | (2006.01) | |
| *H10K 85/60* | (2023.01) | |
| *H10K 50/11* | (2023.01) | |

(52) U.S. Cl.
CPC ............ *C09K 11/06* (2013.01); *C07D 409/10* (2013.01); *C07D 413/10* (2013.01); *H10K 85/657* (2023.02); *H10K 85/6572* (2023.02); *H10K 85/6576* (2023.02); *C09K 2211/1007* (2013.01); *C09K 2211/1018* (2013.01); *H10K 50/11* (2023.02)

(58) Field of Classification Search
CPC ....................................................... C09K 11/06
USPC ........................................................... 544/104
See application file for complete search history.

(56) References Cited

U.S. PATENT DOCUMENTS

2018/0159050 A1    6/2018  Kim

FOREIGN PATENT DOCUMENTS

| CN | 104592194 A | 5/2015 |
|---|---|---|
| CN | 106831744 A | 6/2017 |
| CN | 108794533 A | 11/2018 |
| CN | 109678851 A | 4/2019 |
| CN | 109776490 A | 5/2019 |
| CN | 109970642 A | 7/2019 |

OTHER PUBLICATIONS

Purely Organic Crystals Exhibit Bright Thermally Activated Delayed Fluorescence Authors: Cai Xinyi, Qiao Zhenyang, Li Mengke, Wu Xiao, He Yanmei, Jiang Xiaofang, Cao Yong, Su Shi-jian Publication data:Angewandte Chemie International Edition, published Aug. 5, 2019 ¬Verlag Chemie| : Source info:vol. 58, Nr: 38, pp. 13522-13531.
International Search Report in International application No. PCT/CN2020/090216, dated Sep. 22, 2020.
Written Opinion of the International Searching Authority in International application No. PCT/CN2020/090216, dated Sep. 22, 2020.
Chinese Office Action issued in corresponding Chinese Patent Application No. 202010004429.3 dated Oct. 16, 2020, pp. 1-8.
Advanced Materials» XIE Gaozhan, ETC. Evaporation- and Solution-Process-Feasible Highly Efficient Thianthrene-9,9', 10, 10'-Tetraoxide-Based Thermally Activated Delayed Fluorescence Emitters with Reduced Efficiency Roll-Off, pp. 181-187, published Nov. 9, 2015.
Advanced Materials☐XIE Gaozhan, ETC. Evaporation- and Solution-Process-Feasible Highly Efficient Thianthrene-9,9', 10, 10'-Tetraoxide-Based Thermally Activated Delayed Fluorescence Emitters with Reduced Efficiency Roll-Off.

*Primary Examiner* — Taofiq A Solola
(74) *Attorney, Agent, or Firm* — PV IP PC; Wei Te Chung; Zhigang Ma

(57) ABSTRACT

The invention relates to a high-performance sky blue thermally activated delayed fluorescent material, manufacturing method thereof, and application thereof, which solves the problems of the prior art. Through clever molecular design, a series of sky-blue thermally activated delayed fluorescent materials with less singlet-triplet energy level difference, high luminous efficiency, and fast-rate reverse intersystem crossing constant were synthesized, while fine-tuning of the structure and spectrum thereof were realized.

14 Claims, 1 Drawing Sheet

HIGH-PERFORMANCE SKY BLUE THERMALLY ACTIVATED DELAYED FLUORESCENT MATERIAL, MANUFACTURING METHOD THEREOF, AND APPLICATION THEREOF

RELATED APPLICATIONS

This application is a Notional Phase of PCT Patent Application No. PCT/CN2020/090216 having international filing date of May 14, 2020, which claims the benefit of priority of Chinese Patent Application No. 202010004429.3 filed on Jan. 3, 2020. The contents of the above applications are all incorporated by reference as if fully set forth herein in their entirety.

FIELD OF INVENTION

The invention relates to the field of organic light emitting display (OLED), in particular, to a high-performance sky blue thermally activated delayed fluorescent material, as well as manufacturing method thereof and application thereof.

BACKGROUND OF INVENTION

Organic light emitting diode (OLED) displays do not require a backlight because of their active light emission, and advantages, such as high luminous efficiency, wide viewing angles, fast response times, wide temperature adaptation ranges, relatively simple manufacture process, low driving voltage, less energy consumption, lightness, thinness, and flexible display screen, as well as huge application prospects, so they have attracted the attention of many researchers. In the OLED, the luminescent guest material that plays a leading effect is very important. The luminescent guest materials used in previous OLED were fluorescent materials. Because a ratio of singlet to triplet excitons in the OLED is 1:3, a theoretical internal quantum efficiency (IQE) of the OLED based on the fluorescent materials can only reach 25%, which greatly limits the application of fluorescent electroluminescent devices. Heavy metal complex phosphorescent materials, due to their spin-orbit coupling effect of heavy atoms, can achieve 100% IQE. However, the commonly used heavy metals are precious metals such as iridium (Ir) and platinum (Pt), and the development of heavy metal complex phosphorescent materials for the blue light materials has yet to be overcome. Pure organic thermally activated delayed fluorescence (TADF) materials, with clever molecular design, make molecules have less minimum single-triple energy level difference (ΔEST). In this way, triplet excitons can return to singlet state through reverse intersystem crossing (RISC) and emits light by transitioning to ground state through radiation, so that single and triplet excitons can be used simultaneously, and 100% IQE can also be achieved.

For TADF materials, fast-rate reverse intersystem crossing constant (kRISC) and high photoluminescence quantum yield (PLQY) are necessary conditions for manufacturing of a high-efficiency OLED. Currently, the TADF materials with said conditions are relatively scarce compared to the heavy metal Ir complexes.

Therefore, if a high-performance sky blue thermally activated delayed fluorescent material can be developed to obtain a fluorescent material compound with clever molecular design, to achieve less single and triplet energy level differences, high luminous efficiency, and fast-rate reverse intersystem crossing constant, while enabling fine-tune the structure and spectrum thereof, it will have huge application prospects and economic value.

Technical Problem

An object of the present invention is to provide a high-performance sky blue thermally activated delayed fluorescent material, which realizes ultra-fast reverse intersystem crossing rate and high luminous efficiency.

SUMMARY OF INVENTION

In order to achieve the above object, the high-performance sky blue thermally activated delayed fluorescent material provided by the present invention includes a compound represented by following formula I:

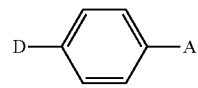

formula I; wherein A is selected from one of following structural formulas:

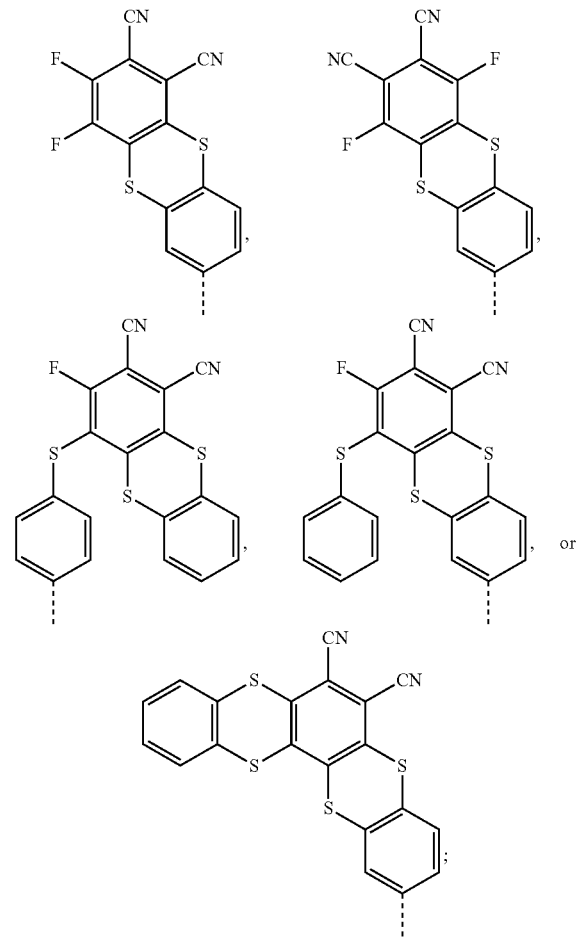

and D is selected from one of following structural formulas:

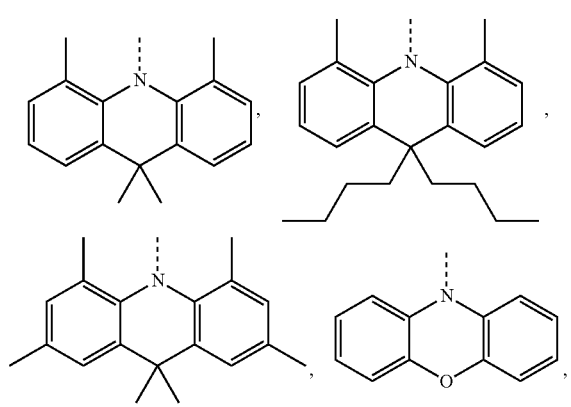

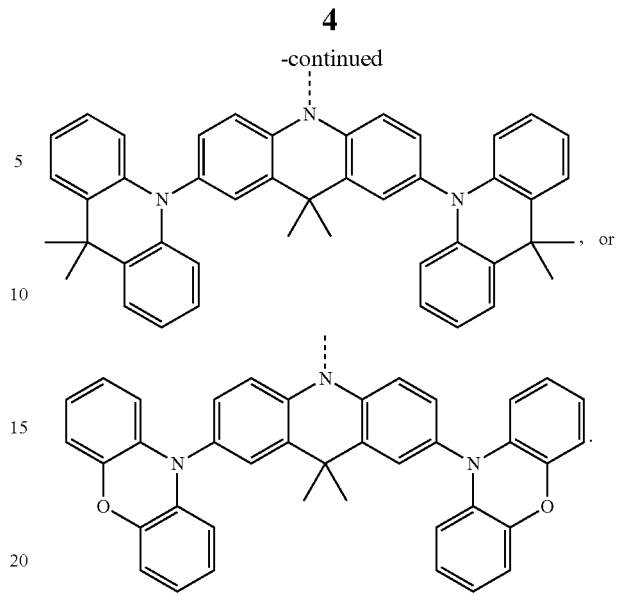

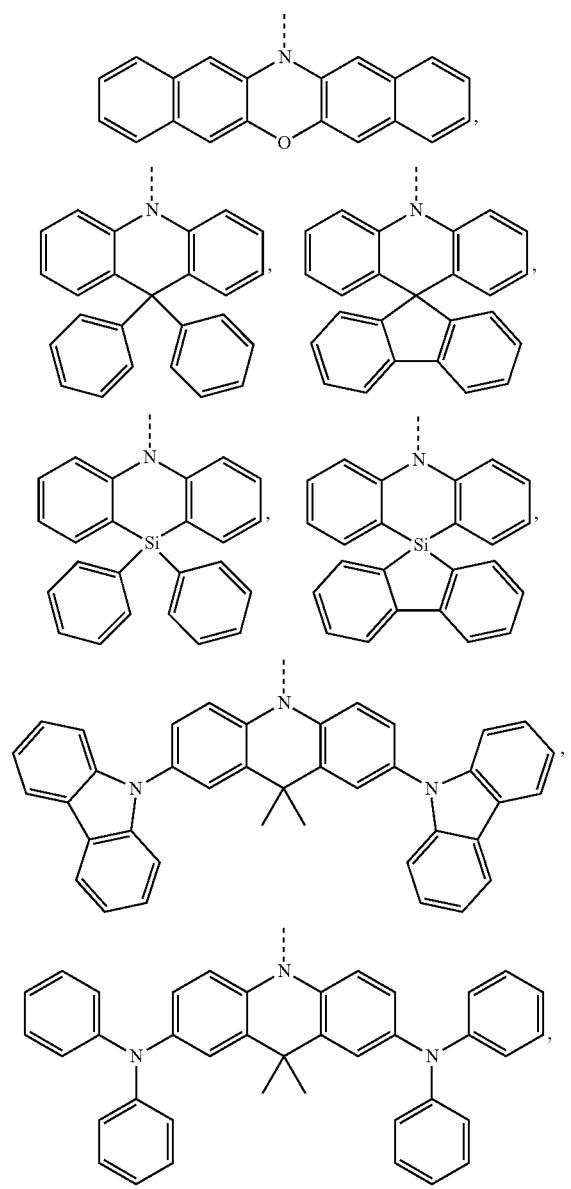

Another object of the present invention is to provide a method of manufacturing the high-performance sky blue thermally activated delayed fluorescent material, including: mixing material 1, material 2, palladium acetate, and tri-tert-butylphosphine tetrafluoroborate to form a solution and adding NaOt—Bu thereto, adding toluene to the solution under argon atmosphere, and subjecting the solution to a reaction to obtain a crude product of the high-performance sky blue thermally activated delayed fluorescent material (i.e. compound represented by the formula I).

Wherein the material 1 is 7-(4-bromophenyl)-3,4-difluorothiophene-1,2-dinitrile.

Wherein the material 2 is phenoxazine, 1,8,9,9'-tetramethylacridine or 1,3,6,8,9,9'-hexamethylacridine.

Wherein a molar ratio of the material 1 to the material 2 is between 1:1 and 1:3, preferably 1:1.2.

Wherein a molar ratio of the palladium acetate to the tri-tert-butylphosphine tetrafluoroborate, and the NaOt—Bu is between 1:3:30 and 1:6:60, preferably 1:3:30.

Wherein a molar volume ratio of the material 1 to the toluene is between 1:5 and 1:20, preferably 1:12 (mmol: mL).

Wherein a reaction temperature of the reaction is between 80° C. and 160° C., preferably 120° C.

Wherein a reaction period of the reaction is between 12 and 48 hours, preferably 24 hours.

The manufacturing method of the high-performance sky blue thermally activated delayed fluorescent material provided by the present invention further includes: cooling the crude product of the high-performance sky blue thermally activated delayed fluorescent material obtained, extracting the crude product with dichloromethane to obtain extracts, combining the extracts with an organic phase solvent, forming silica gel immediately, and performing column chromatography separation and purification process to obtain a high-performance sky blue thermally activated delayed fluorescent material product.

Wherein the method of cooling the crude high-performance sky blue thermally activated delayed fluorescent material is: cooling the crude product to room temperature, and pouring the crude product into ice water.

Wherein, a number of times of extracting with the dichloromethane are between 2 and 4, preferably 3 times.

The manufacturing method of the high-performance sky blue thermally activated delayed fluorescent material provided by the present invention includes: mixing material 1, material 2, palladium acetate and tri-tert-butylphosphine tetrafluoroborate to form a solution and adding NaOt—Bu thereto, adding toluene to the solution under argon atmosphere, and subjecting the solution to a reaction to obtain a crude product of the high-performance sky-blue thermally activated delayed fluorescent material (i.e. compound represented by the formula I). Cooling the crude product of the high-performance sky blue thermally activated delayed fluorescent material obtained to room temperature, pouring the crude product into ice water, and extracting the crude product with dichloromethane to obtain extracts, combining the extracts with an organic phase solvent, forming silica gel immediately, and performing column chromatography separation and purification process to obtain a high-performance sky blue thermally activated delayed fluorescent material product.

Wherein the material 1 is 7-(4-bromophenyl)-3,4-difluorothiophene-1,2-dinitrile.

Wherein the material 2 is phenoxazine, 1,8,9,9'-tetramethylacridine or 1,3,6,8,9,9'-hexamethylacridine.

Wherein a molar ratio of the material 1 to the material 2 is between 1:1 and 1:3, preferably 1:1.2.

Wherein a molar ratio of the palladium acetate to the tri-tert-butylphosphine tetrafluoroborate, and the NaOt—Bu is between 1:3:30 and 1:6:60, preferably 1:3:30.

Wherein a molar volume ratio of the material 1 to the toluene is between 1:5 and 1:20, preferably 1:12 (mmol: mL).

Wherein a reaction temperature of the reaction is between 80° C. and 160° C., preferably 120° C.

Wherein a reaction period of the reaction is between 12 and 48 hours, preferably 24 hours.

Wherein a number of times of extracting with the dichloromethane are between 2 and 4, preferably 3 times.

The manufacturing method of the high-performance sky blue thermally activated delayed fluorescent material provided by the present invention, includes: mixing material 1, material 2, palladium acetate and tri-tert-butylphosphine tetrafluoroborate to form a solution and adding NaOt—Bu thereto, adding toluene to the solution under argon atmosphere, and subjecting the solution to a reaction at 120° C. for 24 hours to obtain a crude product of the high-performance sky-blue thermally activated delayed fluorescent material (i.e. compound represented by the formula I). Cooling the crude product of the high-performance sky blue thermally activated delayed fluorescent material obtained to room temperature, pouring the crude product into ice water, and extracting the crude product with dichloromethane to obtain extracts, combining the extracts with an organic phase solvent, forming silica gel immediately, and performing column chromatography separation and purification process to obtain a high-performance sky blue thermally activated delayed fluorescent material product.

Wherein the material 1 is 7-(4-bromophenyl)-3,4-difluorothiophene-1,2-dinitrile.

Wherein the material 2 is phenoxazine, 1,8,9,9'-tetramethylacridine or 1,3,6,8,9,9'-hexamethylacridine.

Wherein a molar ratio of the material 1 to the material 2 is 1:1.2.

Wherein a molar ratio of the palladium acetate to the tri-tert-butylphosphine tetrafluoroborate, and the NaOt—Bu is 1:3:30.

Wherein a molar volume ratio of the material 1 to the toluene is 1:12 (mmol: mL).

Another object of the present invention is to provide an application of the high-performance sky blue thermally activated delayed fluorescent material.

Wherein the high-performance sky-blue thermally activated delayed fluorescent material is used to manufacture an organic light emitting display (OLED), more specifically, to manufacture a light-emitting layer of the OLED.

The present invention has following beneficial effects:
(1) Through matching of different functional groups, the sky blue TADF materials with significant TADF characteristics are designed.
(2) Reasonable synthetic route design, material synthesis efficiency is improved.
(3) The manufacturing of high-efficiency organic electroluminescent devices is realized.
(4) Display devices and electronic devices based on the organic light-emitting material can be manufactured.

TADF material has a molecular structure combining electron donor (D) and electron acceptor (A). The present invention regulates the structure of the electron donor/acceptor unit to change its electron-donating/electron-accepting ability, therefore effectively increases the luminous efficiency of the materials. At the same time, researches the influence of the magnitude of the charge transfer state on the material properties. Finally, the electroluminescent devices based on the target sky blue TADF materials have achieved very high efficiency.

BENEFICIAL EFFECT

In conclusion, the present invention solves the problems of the prior art. Through clever molecular design, a series of sky blue thermally activated delayed fluorescent materials with less singlet-triplet energy level difference, high luminous efficiency, and fast-rate reverse intersystem crossing constant were synthesized, while realizing fine-tune the structure and the spectrum thereof. Using mass spectrometry analysis to confirm their structures, and carried out detailed research on their photophysical properties, and finally applied these sky blue TADF materials to the luminescent layer to manufacture a series of high-performance OLED, which have huge application prospects and economics value.

DETAILED DESCRIPTION OF PREFERRED EMBODIMENTS

Figure 1:
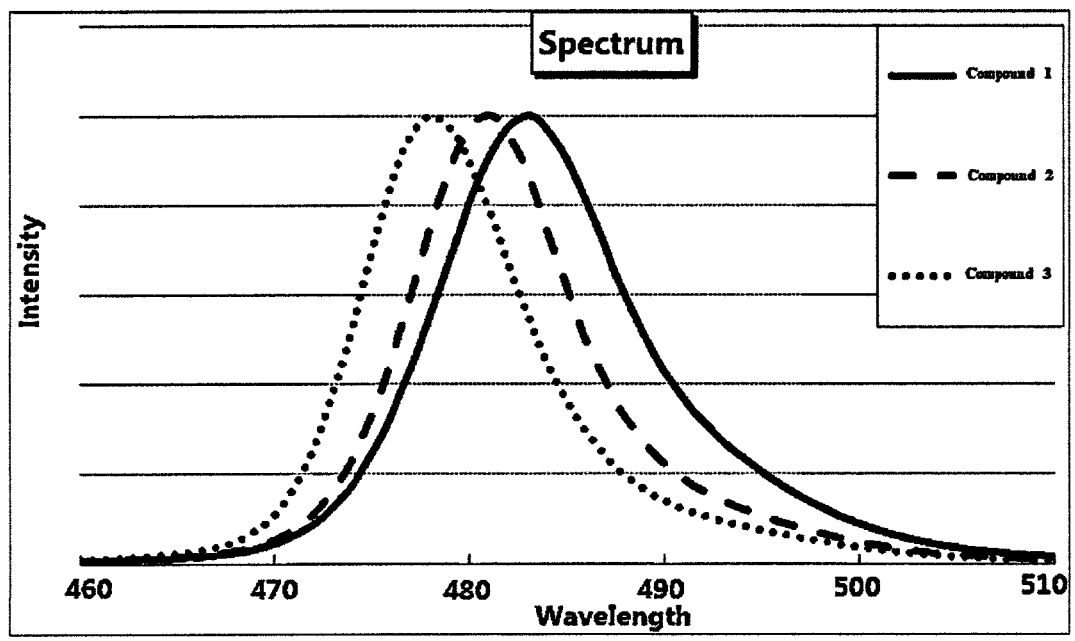
FIG. 1 is a photoluminescence spectrum chart of a target molecule in embodiment 1.

The following embodiments are used to illustrate the present invention but are not used to limit the scope of the present invention.

The operations that are not mentioned in the present invention are all conventional operations in the art, and the materials that are not mentioned in the present invention are all conventional materials that are commercially available.

Source of materials:

The material 1 used in the present invention is 7-(4-bromophenyl)-3,4-difluorothiophene-1,2-dinitrile, and the intermediate is self-synthesized.

The terms appearing in the present invention are explained as follows: organic light emitting diode (OLED) displays, high effectiveness (High Efficiency), long life (Long Lifetime).

The high-performance sky blue thermally activated delayed fluorescent material provided by the present invention is a compound represented by formula I in the specification, where groups A and D can be substituted to obtain the following three compounds:

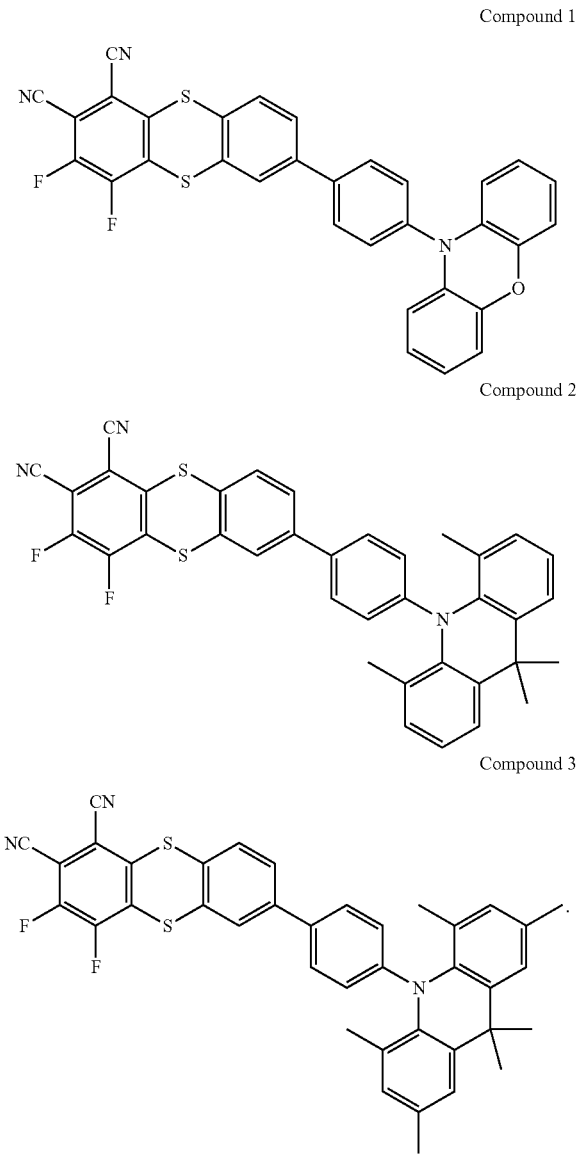

The method of manufacturing the high-performance sky blue thermally activated delayed fluorescent material provided by the present invention includes: mixing material 1 (7-(4-bromophenyl)-3,4-difluorothiophene-1,2-dinitrile), material 2 (phenoxazine, 1,8,9,9'-tetramethylacridine or 1,3,6,8,9,9'-hexamethylacridine; a molar ratio of the material 1 to the material 2 is between 1:1 and 1:3, preferably 1:1.2), palladium acetate, and tri-tert-butylphosphine tetrafluoroborate to form a solution and adding NaOt—Bu thereto (a molar ratio of the palladium acetate to the tri-tert-butylphosphine tetrafluoroborate, and to the NaOt—Bu is between 1:3:30 and 1:6:60, preferably 1:3:30), and adding toluene to the solution under argon atmosphere (a molar volume ratio of the material 1 to the toluene is between 1:5 and 1:20, preferably 1:12, the unit is mmol:mL), and subjecting the solution to a reaction (temperature of the reaction is between 80° C. and 160° C., preferably 120° C.; and period of the reaction is between 12 and 48 hours, preferably 24 hours.) to obtain a crude product of the high-performance sky blue thermally activated delayed fluorescent material (i.e. compound represented by the formula I above); cooling the crude product of the high-performance sky blue thermally activated delayed fluorescent material obtained to room temperature, pouring the crude product into ice water, and extracting the crude product with dichloromethane (the numbers of times is between 2 and 4, preferably 3 times) to obtain extracts, combining the extracts with an organic phase solvent, forming silica gel immediately, and performing column chromatography separation and purification process to obtain a high-performance sky blue thermally activated delayed fluorescent material product.

Embodiment 1

Synthetic route of the target compound 1 is as follows:

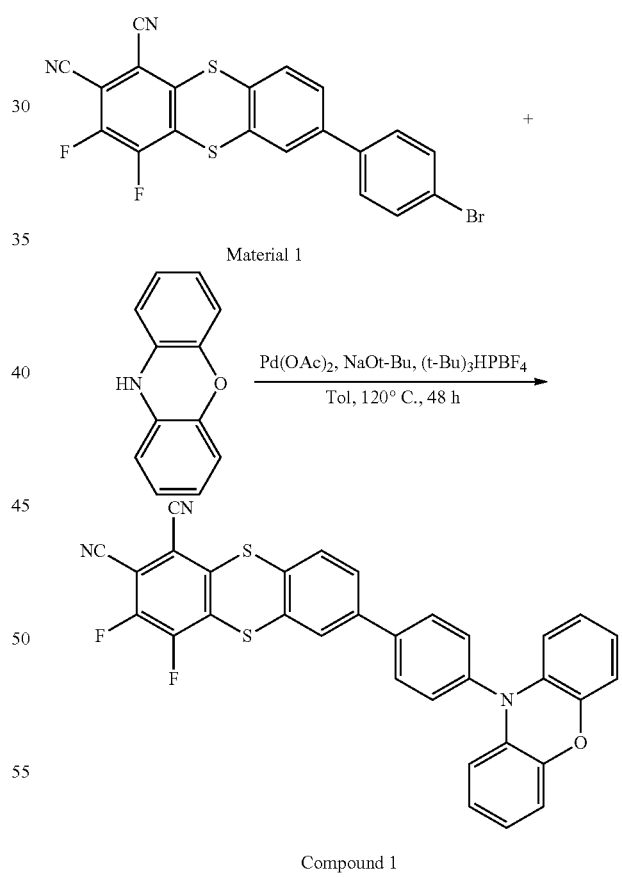

Synthesis steps:

Material 1 (2.3 g, 5 mmol), phenoxazine (1.1 g, 6 mmol), palladium acetate (45 mg, 0.2 mmol) and tri-tert-butylphosphine tetrafluoroborate (0.17 g, 0.6 mmol) were added to a two-neck flask (100 mL). Then, NaOt—Bu (0.58 g, 6 mmol) was added to the glove box, and toluene of 60 mL that had been previously dehydrated and deoxygenated was added under argon atmosphere and reacted at 120° C. for 24 hours. After cooling to room temperature, the reaction solution was poured into ice water of 200 mL, extracted three times with dichloromethane to obtain extracts, combining the extracts with an organic phase solvent, forming silica gel immediately, and performing column chromatography (dichloromethane:n-hexane, v:v, 1:2) separation and purification process to obtain a light blue powder of 1.3 g, yield: 47%. MS (EI) m/z: 559.01.

Embodiment 2

Synthetic route of the target compound 2 is as follows:

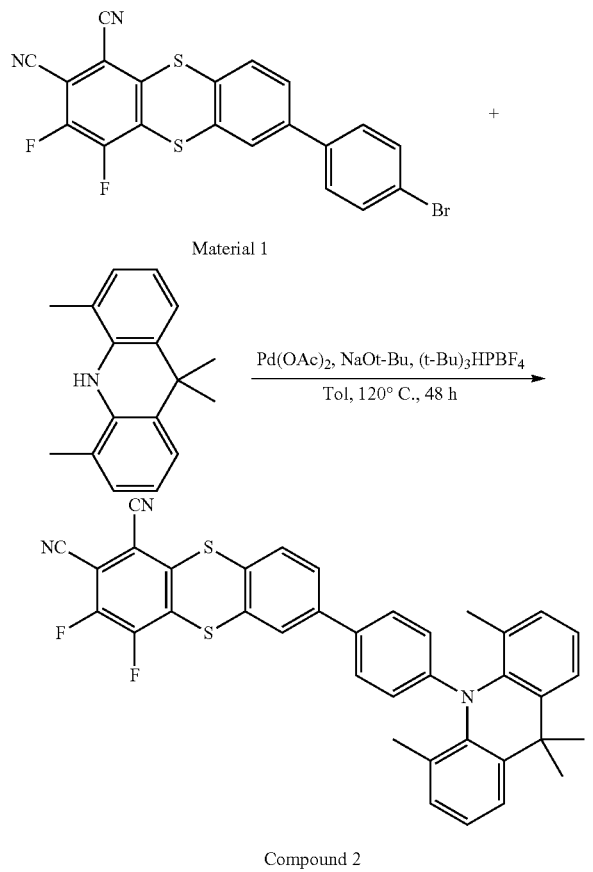

Compound 2

Synthesis steps:

Material 1 (2.3 g, 5 mmol), 1,8,9,9'-tetramethylacridine (1.4 g, 6 mmol), palladium acetate (45 mg, 0.2 mmol) and tri-tert-butylphosphine tetrafluoroborate (0.17 g, 0.6 mmol) were added to a two-neck flask of 100 mL. Then, NaOt—Bu (0.58 g, 6 mmol) was added to the glove box, and toluene of 60 mL that had been previously dehydrated and deoxygenated was added under argon atmosphere and reacted at 120° C. for 24 hours. After cooling to room temperature, the reaction solution was poured into ice water of 200 mL, extracted with dichloromethane for three times to obtain extracts, combining the extracts with an organic phase solvent, forming silica gel immediately, and performing column chromatography (dichloromethane:n-hexane, v:v, 3:2) separation and purification process to obtain a light blue powder of 1.1 g, yield: 34%. MS (EI) m/z: 613.08.

Embodiment 3

Synthetic route of the target compound 3 is as follows:

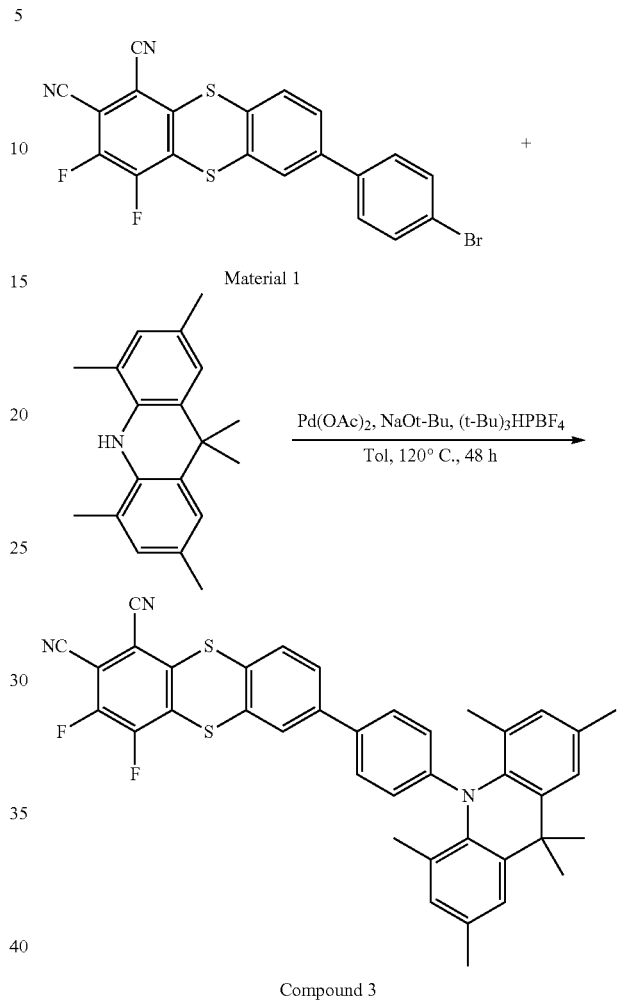

Compound 3

Synthesis steps:

Material 1 (2.3 g, 5 mmol), 1,3,6,8,9,9'-hexamethylacridine (1.6 g, 6 mmol), palladium acetate (45 mg, 0.2 mmol) and tri-tert-butylphosphine tetrafluoroborate (0.17 g, 0.6 mmol) were added to a two-neck flask of 100 mL. Then, NaOt—Bu (0.58 g, 6 mmol) was added to the glove box, and toluene of 60 mL that had been previously dehydrated and deoxygenated was added under argon atmosphere and reacted at 120° C. for 24 hours. After cooling to room temperature, the reaction solution was poured into ice water of 200 mL, extracted with dichloromethane for three times to obtain extracts, combining the extracts with an organic phase solvent, forming silica gel immediately, and performing column chromatography (dichloromethane:n-hexane, v:v, 3:2) separation and purification process to obtain a light blue powder of 1.2 g, yield: 37%. MS (EI) m/z: 641.00.

Experimental Example 1

The lowest singlet energy level (S1) and lowest triplet energy level (T1) of the target molecules (i.e. compound 1, compound 2, and compound 3) are shown in the table below:

| | PL Peak (nm) | $S_1$ (eV) | $T_1$ (eV) | $\Delta E_{ST}$ (eV) | HOMO (eV) | LUMO (eV) |
|---|---|---|---|---|---|---|
| Compound 1 | 486 | 2.55 | 2.43 | 0.12 | −5.43 | −2.64 |
| Compound 2 | 482 | 2.57 | 2.40 | 0.17 | −5.61 | −2.61 |
| Compound 3 | 476 | 2.61 | 2.41 | 0.20 | −5.64 | −2.62 |

The photophysical properties of the target molecules (i.e. compound 1, compound 2, and compound 3): at room temperature, a photoluminescence spectrum of the target molecules in the toluene solution is shown in FIG. 1, wherein horizontal axis refers to wavelength and vertical axis refers to normalized intensity.

Experimental Example 2

An electro-thermally activated delayed fluorescent device using the thermally activated delayed fluorescent material of the invention as a light-emitting layer, which may include glass or conductive glass (ITO) substrate layer 1, a hole injection layer 2 (MoO$_3$), a hole transport layer 3 (TCTA), a light-emitting layer 4 (DPERO: sky blue material with delayed fluorescence of the invention), an electron transport layer 5 (1,3,5-tris (3-(3-pyridyl)phenyl)benzene Tm3PyPB), and a cathode layer 6 (fluorine lithium/aluminum). The schematic diagram of the electroluminescent device is shown in FIG. 2.

The electroluminescent device can be manufactured based on a method known in the art, such as the method disclosed in the reference (Adv. Mater. 2003, 15, 277.). The specific method is: MoO$_3$, TCTA, DPERO+thermally activated delayed fluorescent material, TmPyPB, LiF of 1 nm, and Al of 100 nm were deposited on a cleaned conductive glass (ITO) substrate under high vacuum.

Figure 2:
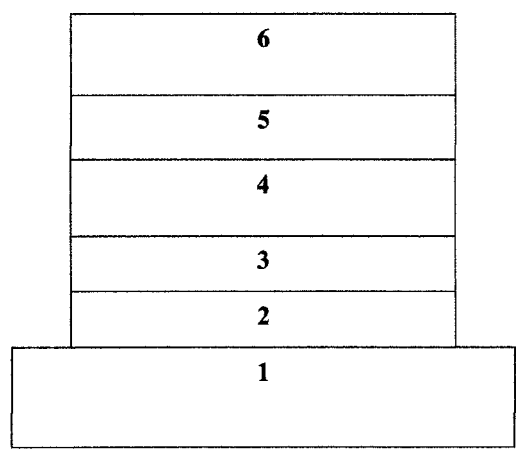
FIG. 2 is a schematic diagram of an electroluminescent device in embodiment 2.

The device shown in FIG. 2 is manufactured by this method, and various specific device structures are as follows:

Device 1 (A1): ITO/MoO$_3$ (2 nm)/TCTA (35 nm)/DPEPO: compound 1 (10%, 20 nm)/Tm3PyPB (40 nm)/LiF (1 nm)/Al (100 nm).

Device 2 (A2): ITO/MoO$_3$ (2 nm)/TCTA (35 nm)/DPEPO: compound 2 (10%, 20 nm)/Tm3PyPB (40 nm)/LiF (1 nm)/Al (100 nm).

Device 3 (A3): ITO/MoO$_3$ (2 nm)/TCTA (35 nm)/DPEPO: compound 3 (10%, 20 nm)/Tm3PyPB (40 nm)/LiF (1 nm)/Al (100 nm).

The current-brightness-voltage characteristics of the device are completed by Keithley source measurement system (Keithley 2400 Sourcemeter, Keithley 2000 Currentmeter) with a corrected silicon photodiode. The electroluminescence spectrum is measured by SPEX CCD3000 spectrometer of French JY Company. All measurements are done at room temperature in the atmosphere.

The performance data of the device is shown in the table below:

| Device | Maximum current efficiency (cd/A) | CIEx, CIEy | Maximum external quantum efficiency (%) |
|---|---|---|---|
| Device 1 | 25.7 | (0.15, 0.28) | 17.1 |
| Device 2 | 23.8 | (0.15, 0.25) | 16.9 |
| Device 3 | 19.5 | (0.15, 0.20) | 15.8 |

Fields of Application of the Invention:
(1) High-efficiency sky blue TADF material;
(2) Long-life sky blue electroluminescent device; and
(3) Display based on electroluminescent devices.

Although the present invention has been described in detail with the general description and specific embodiments above, on the basis of the present invention, some modifications or improvements can be made, which is obvious to those skilled in the art. Therefore, these modifications or improvements made on the basis of not deviating from the spirit of the present invention shall fall within the protection scope of the present invention.

Industrial Applicability

The subject matter of the present application can be manufactured and used in industry, and therefore has industrial applicability.

What is claimed is:
1. A high-performance sky blue thermally activated delayed fluorescent material, comprising a compound represented by following formula I:

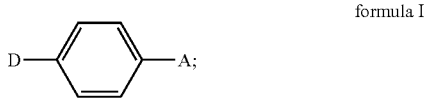

wherein A is selected from one of following structural formulas:

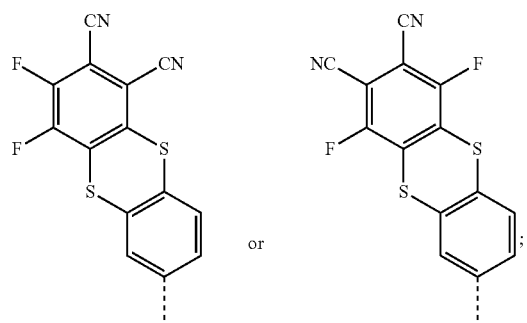

and
D is selected from one of following structural formulas:

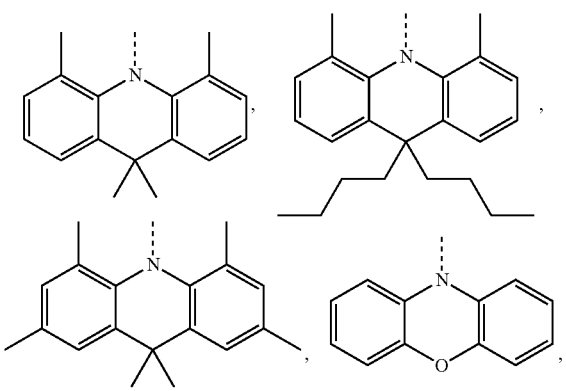

-continued

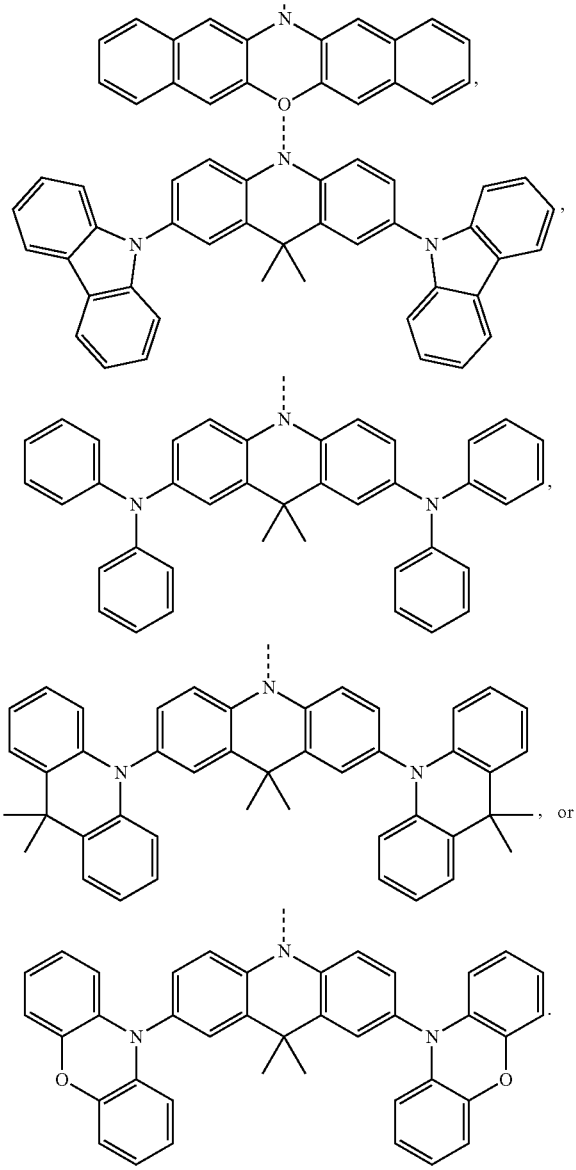

2. A method of manufacturing the high-performance sky blue thermally activated delayed fluorescent material according to claim 1, comprising:
mixing material 1, material 2, palladium acetate, and tri-tert-butylphosphine tetrafluoroborate to form a solution and adding NaOt-Bu thereto, adding toluene to the solution under argon atmosphere, and subjecting the solution to a reaction to obtain a crude product of the high-performance sky blue thermally activated delayed fluorescent material represented by the formula I; wherein the material 1 is 7-(4-bromophenyl)-3,4-difluorothiophene-1,2-dinitrile; and the material 2 is phenoxazine, 1,8,9,9'-tetramethylacridine or 1,3,6,8,9,9'-hexamethylacridine.

3. The method of manufacturing the high-performance sky blue thermally activated delayed fluorescent material according to claim 2, wherein a molar ratio of the material 1 to the material 2 is between 1:1 and 1:3.

4. The method of manufacturing the high-performance sky blue thermally activated delayed fluorescent material according to claim 2, wherein a molar ratio of the material 1 to the material 2 is 1:1.2.

5. The method of manufacturing the high-performance sky blue thermally activated delayed fluorescent material according to claim 2, wherein a molar ratio of the palladium acetate to the tri-tert-butylphosphine tetrafluoroborate, and the NaOt-Bu is between 1:3:30 and 1:6:60.

6. The method of manufacturing the high-performance sky blue thermally activated delayed fluorescent material according to claim 2, wherein a molar ratio of the palladium acetate, the tri-tert-butylphosphine tetrafluoroborate, and the NaOt-Bu is 1:3:30.

7. The method of manufacturing the high-performance sky blue thermally activated delayed fluorescent material according to claim 2, wherein a molar volume ratio of the material 1 to the toluene is between 1:5 and 1:20.

8. The method of manufacturing the high-performance sky blue thermally activated delayed fluorescent material according to claim 2, wherein a molar volume ratio of the material 1 to the toluene is 1:12.

9. The method of manufacturing the high-performance sky blue thermally activated delayed fluorescent material according to claim 2, wherein a reaction temperature of the reaction is between 80° C. and 160° C.; and a reaction period of the reaction is between 12 and 48 hours.

10. The method of manufacturing the high-performance sky blue thermally activated delayed fluorescent material according to claim 2, wherein a reaction temperature of the reaction is 120 cc; and a reaction period of the reaction is 24 hours.

11. The method of manufacturing the high-performance sky blue thermally activated delayed fluorescent material according to claim 2, further comprising: cooling the crude product of the high-performance sky blue thermally activated delayed fluorescent material obtained, extracting the crude product with dichloromethane to obtain extracts, combining the extracts with an organic phase solvent, forming silica gel immediately, and performing column chromatography separation and purification process to obtain a high-performance sky blue thermally activated delayed fluorescent material product.

12. A method of manufacturing the high-performance sky blue thermally activated delayed fluorescent material according to claim 1, comprising:
mixing material 1, material 2, palladium acetate and tri-tert-butylphosphine tetrafluoroborate to form a solution and adding NaOt-Bu thereto, adding toluene to the solution under argon atmosphere, and subjecting the solution to a reaction to obtain a crude product of the high-performance sky-blue thermally activated delayed fluorescent material represented by the formula I; cooling the crude product of the high-performance sky blue thermally activated delayed fluorescent material obtained to room temperature, pouring the crude product into ice water, and extracting the crude product with dichloromethane to obtain extracts, combining the extracts with an organic phase solvent, forming silica gel immediately, and performing column chromatography separation and purification process to obtain a high-performance sky blue thermally activated delayed fluorescent material product; wherein the material 1 is 7-(4-bromophenyl)-3,4-difluorothiophene-1,2-dinitrile; and the material 2 is phenoxazine, 1,8,9,9'-tetramethylacridine or 1,3,6,8,9,9'-hexamethylacridine; a molar ratio of the material 1 to the material 2 is between 1:1 and 1:3; a molar ratio of the palladium acetate to the tri-tert-butylphosphine tetrafluoroborate, and the NaOt-Bu is between 1:3:30 and 1:6:60; a molar volume ratio of the material 1 to the toluene is between 1:5 and 1:20; a reaction temperature of the reaction is between 80° C. and 160° C.; a reaction period of the reaction is between 12 and 48 hours; and a number of times of the extracting with the dichloromethane are between 2 and 4.

13. An application of the high-performance sky blue thermally activated delayed fluorescent material according to claim 1.

14. The application of the high-performance sky-blue thermally activated delayed fluorescent material according to claim 13, wherein the high-performance sky-blue thermally activated delayed fluorescent material is used to manufacture an organic light emitting display.

* * * * *